United States Patent
Zuend et al.

(10) Patent No.: US 12,195,496 B2
(45) Date of Patent: *Jan. 14, 2025

(54) 2'-DEOXY-2',2'-DIFLUOROTETRAHYDROURIDINES WITH HIGH PURITY AND METHODS OF MAKING THE SAME

(71) Applicant: Otsuka Pharmaceutical Co., Ltd., Tokyo (JP)

(72) Inventors: Gemma Zuend, Haywood, CA (US); Ian Scott, Niwot, CO (US); Nipun Davar, Pleasanton, CA (US); Kimiyoshi Annaka, Osaka (JP); Masahiro Miyake, Osaka (JP); Motoshi Matsui, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/309,435

(22) Filed: Apr. 28, 2023

(65) Prior Publication Data

US 2023/0303609 A1    Sep. 28, 2023

Related U.S. Application Data

(63) Continuation of application No. 17/766,074, filed as application No. PCT/US2020/054500 on Oct. 7, 2020.

(60) Provisional application No. 62/912,317, filed on Oct. 8, 2019.

(51) Int. Cl.
*C07H 19/06* (2006.01)
*C07H 1/00* (2006.01)

(52) U.S. Cl.
CPC ............... *C07H 19/06* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 8,268,800 B2 * | 9/2012 | Hamilton | A61P 35/04 536/28.4 |
| 9,834,576 B2 | 12/2017 | Choi et al. | |
| 2019/0076464 A1 | 3/2019 | Cordelier et al. | |

FOREIGN PATENT DOCUMENTS

| | | |
|---|---|---|
| CN | 101827856 A | 9/2010 |
| CN | 109999038 A | 7/2019 |
| JP | 2011500713 A | 1/2011 |
| JP | 2017500281 A | 1/2017 |
| WO | 2009052287 A1 | 4/2009 |
| WO | 2015066162 A1 | 5/2015 |

OTHER PUBLICATIONS

Campagne, Michiel M. Van Lookeren, and Peter JM Van Haastert. "A sensitive cyclic nucleotide phosphodiesterase assay for transient enzyme kinetics." Analytical Biochemistry 135.1 (1983): 146-150.*
"International Preliminary Report on Patentability corresponding to International Application No. PCT/2020/054500 mailed Apr. 21, 2022".
"International Search Report and Written Opinion corresponding to International Application No. PCT/2020/054500 mailed Feb. 4, 2021".
"Third Party observations corresponding to International Application No. PCT/US2020/054500 dated Feb. 8, 2022".
Ferraris, Dana , et al., "Design, Synthesis, and Pharmacological Evaluation of Fluorinated Tetrahydrouridine Derivatives as Inhibitors of Cytidine Deaminase", Journal of Medicinal Chemistry 57(6):2582-2588 (Feb. 12, 2014).
"U.S. Appl. No. 17/766,074; office action mailed Mar. 7, 2024".
"Extended European Search Report corresponding to European Application No. 20874994.5 dated Feb. 12, 2024".
Romanski, et al., "High-pressure transesterification of sterically hindered esters", Tetrahedron Letters 53:5287-5289 (Jul. 27, 2012).

* cited by examiner

*Primary Examiner* — Patrick T Lewis
(74) *Attorney, Agent, or Firm* — Myers Bigel, P.A.

(57) ABSTRACT

The invention relates to methods of synthesizing 2'-deoxy-2',2'-difluorotetrahydrouridine with increased purity and uniform particle size distribution. In particular, methods of the invention include crystallization and isolation procedures rendering synthetic reaction intermediates. The invention further includes compositions comprising the final compound in highly pure form, including lower number of impurities and lower levels of individual and total impurities.

6 Claims, No Drawings

2'-DEOXY-2',2'-DIFLUOROTETRAHYDROURIDINES WITH HIGH PURITY AND METHODS OF MAKING THE SAME

STATEMENT OF PRIORITY

This application is a continuation of and claims priority to U.S. patent application Ser. No. 17/766,074, filed Apr. 1, 2022, which is a 35 U.S.C. § 371 national phase application of PCT Application PCT/US2020/054500 filed Oct. 7, 2020, which claims the benefit, under 35 U.S.C. § 119(e), of U.S. Provisional Application Ser. No. 62/912,317, filed on Oct. 8, 2019, the entire contents of each of which are incorporated by reference herein in their entireties.

FIELD OF INVENTION

The invention relates to methods of synthesizing 2'-deoxy-2',2'-difluorotetrahydrouridine with increased purity and uniform particle size distribution. In particular, methods of the invention include crystallization and isolation procedures rendering synthetic reaction intermediates as well as the final compound in highly pure form.

BACKGROUND OF INVENTION

Several important chemotherapeutic compounds are analogs of the nucleotide cytidine, including decitabine, gemcitabine, 5-azacytidine, ara-C, tezacitabine, 5-fluoro-2'-deoxycytidine, and cytochlor. As analogs of cytidine, the compounds are subject to degradation by the enzyme cytidine deaminase (CDA) which degrades the compounds into inactive metabolites. The presence of CDA limits the effectiveness of the cytidine analogs, requiring the administration of higher and/or more frequent doses of the analogs to achieve therapeutic benefit.

One approach to overcoming this problem is to co-administer a CDA inhibitor with the cytidine analog, thereby blocking degradation of the analog. One class of CDA inhibitor is 2'-deoxy-2',2'-difluorotetrahydrouridine compounds. U.S. Pat. No. 8,268,800, incorporated herein by reference in its entirety, discloses compounds in this class, including compound 1:

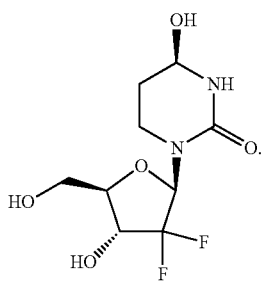

A need exists for more efficient processes for producing CDA inhibitors such as 2'-deoxy-2',2'-difluorotetrahydrouridine for use in methods of treating cancer and other disorders.

SUMMARY OF EMBODIMENTS OF THE INVENTION

The present invention relates to the development of a more efficient method for synthesizing 2'-deoxy-2',2'-difluorotetrahydrouridine compounds and intermediates involved in the synthesis. Previous synthetic methods in the art were inconvenient due to the use of an inefficient transfer hydrogenation process and the use of preparative HPLC to isolate the final compound. The inventors of the present invention developed a synthetic method with improved efficiency which achieved the ability of the final compound to be purified by precipitation or crystallization, e.g., crystallization-induced diastereoselective transformation (CIDT) which converts the mixture of epimers to the desired compound and hence results in enhanced yield of the desired epimer (see WO 2015/066162). The present invention improves on this method by reducing impurities, improving yield, shortening reaction time, and/or otherwise improving conditions for production at industrial scale.

Another aspect of the invention relates to a method of producing compound 1 (named (4R)-1-[(2R,4R,5R)-3,3-difluoro-4-hydroxy-5-(hydroxymethyl)tetrahydrofuran-2-yl]-4-hydroxytetrahydropyrimidin-2(1H)-one)):

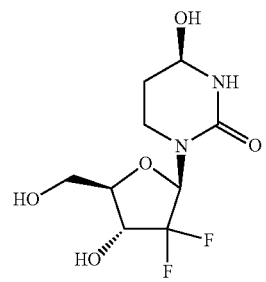

or a salt thereof;
comprising the steps of:
(a) hydrogenating the starting compound of Formula IV:

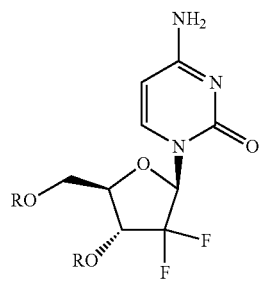

wherein R is a hydroxyl protecting group,
to produce the compound of Formula IIa:

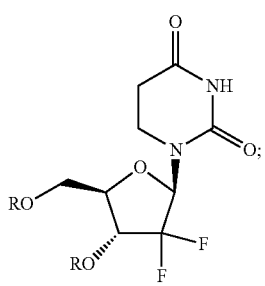

(b) reducing the compound of Formula IIa to produce the compound of Formula IIIa:

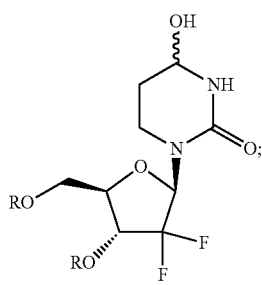

IIIa (c) deprotecting the compound of Formula IIIa to produce compound 2:

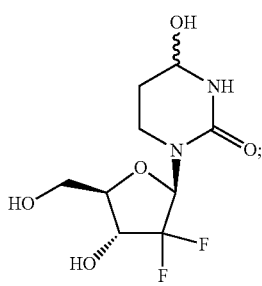

2 and
(d) precipitating or crystallizing compound 2 in the presence of a catalyst to produce compound 1:

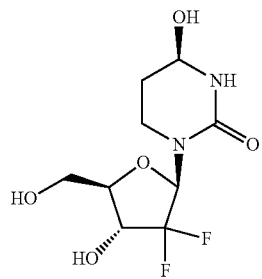

1 or a salt thereof;
wherein the method comprises one or more of the following in any combination:
(i) wherein the hydrogenating step (a) is performed under hydrogen atmosphere with a palladium catalyst;
(ii) wherein the reducing step (b) is performed at a temperature of about −12° C. to about −5° C.;
(iii) wherein the deprotecting step (c) is performed in the presence of an organic base; and/or
(iv) wherein the work-up of the deprotected compound from deprotecting step (c) is performed under non-aqueous conditions. In some embodiments, the present invention further comprises a step wherein the final product is recrystallized and the recrystallizing is performed at a pH of about 6.0 to about 7.4 and carried out by dissolving the final product at a temperature of about 50° C. to about 55° C. to produce a solution and then cooling the solution to about 5° C.

A further aspect of the invention relates to high purity compound 1 (for example compound 1 having a purity of at least about 80%, e.g., at least about 85%, 90%, 95%, 96%, 97%, 98%, 99%, 99.5%, or 99.9%):

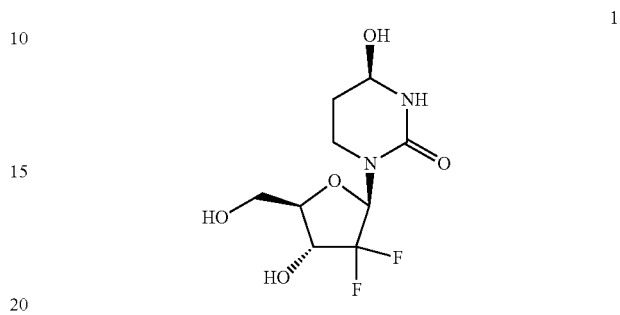

1 or a salt thereof. The high purity compound 1 may be produced by the methods of the invention. Other aspects of the invention relate to compound 1 comprising a lower number of impurities and/or lower levels of individual impurities and total impurities compared to compound 1 produced by prior methods.

DETAILED DESCRIPTION OF EMBODIMENTS OF THE INVENTION

The present invention now will be described hereinafter with reference to the accompanying examples, in which embodiments of the invention are shown. This invention may, however, be embodied in many different forms and should not be construed as limited to the embodiments set forth herein.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

For purposes herein, if there is any ambiguity as between a written chemical name and a drawn chemical structure, the drawn chemical structure will control.

Definitions

As used herein, "a," "an," or "the" can mean one or more than one. For example, "a" compound can mean a single compound or a multiplicity of compounds.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a compound) and the like, is meant to encompass variations of ±10%, 5%, 1%, 0.5%, or even ±0.1% of the specified amount.

The terms "comprise," "comprises," and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim or the description of this invention is not intended to be interpreted to be equivalent to "comprising."

As used herein, the terms "increase," "increases," "increased," "increasing," and similar terms indicate an elevation of at least about 25%, 50%, 75%, 100%, 150%, 200%, 300%, 400%, 500% or more.

As used herein, the terms "reduce," "reduces," "reduced," "reduction," and similar terms mean a decrease of at least about 5%, 10%, 15%, 20%, 25%, 35%, 50%, 75%, 80%, 85%, 90%, 95%, 97% or more. In particular embodiments, the reduction results in no or essentially no (i.e., an insignificant amount, e.g., less than about 10% or even 5%) detectable activity or amount.

The term "salt thereof" includes pharmaceutically acceptable salts. The term "pharmaceutically acceptable salts" shall mean non-toxic salts of the compounds employed in this invention which are generally prepared by reacting the free acid with a suitable organic or inorganic base or the free base with a suitable organic or inorganic acid. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamoate, palmitate, panthothenate, phosphate/diphosphate, polygalacturonate, potassium, salicylate, sodium, stearate, subacetate, succinate, tannate, tartrate, teoclate, tosylate, triethiodide, and valerate.

The term "Bronsted-Lowry base" as used herein refers to a species with the ability to accept a proton.

The term "hydroxyl protecting group" as used herein may be any suitable hydroxyl protecting group, i.e., a labile chemical moiety which is known in the art to protect a hydroxyl group against undesired reactions during synthetic procedures. After said synthetic procedure(s) the blocking group as described herein may be selectively removed. See, e.g., A. Isidro-Llobet et al., Amino Acid-Protecting Groups, Chem. Rev. 109:2455-2504 (2009) and T. Greene and P. Wuts, *Protective Groups in Organic Synthesis* (3d Ed. 1999). In some embodiments, the hydroxyl protecting group is an acid-stabile hydroxyl protecting group. Examples of hydroxyl protecting groups include, but are not limited to, alkyl, cycloalkyl, arylalkyl, aryl, ethers, esters, cyclic ethers, cyclic esters, acetal, cyclic acetal, ketal, and cyclic ketal groups and the like that can be removed under either acidic or basic conditions so that the protecting group is removed and replaced with a hydrogen atom. Specific hydroxyl protecting groups include, but are not limited to, methyl, ethyl, acetate, ethylacetate, propionate, ethylene glycol, propylene glycol, 4-methoxybenzyl, benzyl, trityl, trimethylsilyl, tetrahydropyranyl, and benzoyl. Other hydroxyl protecting groups include, but are not limited to, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate(mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec); 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate(mesylate), benzylsulfonate, and tosylate (Ts). Methods of protecting and deprotecting hydroxyl groups, are well known and, for example, can be found in Protective Groups in Organic Synthesis (T. Green and P. Wuts; 3rd Edition; John Wiley and Sons, 1999).

A bond identified by "------" is either present or absent.

A bond identified by "〜〜" is one that includes a mixture of stereochemistries.

The term "g/g" as used herein refers to gram per gram of substrate. The substrate is defined as 1 equivalent in each step and all other aspects within the step are defined relative to the substrate.

The term "enantiomers" refers to stereoisomers of a compound that are mirror images of each other and are non-superimposable. In the application, unless otherwise mentioned or indicated, the chemical designation of compounds denotes the mixture of all possible stereochemically isomeric forms.

The term "diastereomers" refers to stereoisomers of a compound that have different configurations at one or more stereocenters but are not mirror images of each other (and therefore not enantiomers).

The term "epimers" refers to two diastereomers that differ from each other at only one stereocenter.

The term "alkyl" denotes a straight or branched hydrocarbon chain containing 1-12 carbon atoms, e.g., 1-6 or 1-4 carbon atoms. Examples of alkyl groups include methyl, ethyl, propyl, isopropyl, butyl, isobutyl, tert-butyl, and the like.

The term "aryl" refers to an aromatic 5-8 membered monocyclic or 8-12 membered bicyclic ring system. The term also includes aromatic bicyclic ring systems in which a hydrogen atom has been added to one, two, or three of the ring carbons in one of the rings (e.g., a partially saturated ring). Examples of aryl groups include phenyl, naphthyl and the like.

The term "acyl" denotes an alkyl or aryl group linked to a carbonyl group. Examples of acyl groups include formyl, acetyl, propionyl, acrylyl, benzoyl, and the like.

The term "benzoyl," as used herein, refers to the acyl of benzoic acid (attached through the carbonyl carbon) and has the following structure.

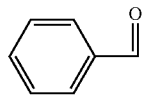

Compounds

One aspect of the invention relates to compound 1 (or salt thereof) produced by the methods of the present invention, in particular compound 1 in free base form having high purity (for example epimeric purity or low amounts of impurities, solvents, reaction side products and/or degradation products). Another aspect of the invention relates to compound 1 having a purity of at least about 80%, e.g., at least about 85%, 90%, 95%, 96%, 97%, 98%, 99%, 99.5%, or 99.9% by weight, or more. In some embodiments, compound 1 contains less than about 20%, e.g., less than about 15%, 10%, 5%, 4%, 3%, 2%, 1%, 0.9%, 0.8%, 0.7%, 0.6%, 0.5%, 0.4%, 0.3%, 0.2%, or 0.1% by weight of impurities, solvents, reaction side products and/or degradation products, e.g., the impurities shown in Table 1 and Table 4 below. In some embodiments, compound 1 contains less than about 20%, e.g., less than about 15%, 10%, 5%, 4%, 3%, 2%, 1%, 0.9%, 0.8%, 0.7%, 0.6%, 0.5%, 0.4%, 0.3%, 0.2%, or 0.1% by weight of its corresponding enantiomer and/or an epimer of compound 1. A further aspect of the invention relates to compound 1 having a molar ratio of the desired epimer (compound 1) to the other epimer (compound 6) of at least about 60:40, e.g., at least about 70:30, 80:20, 90:10, 95:5, 96:4, 97:3, 98:2, 99:1 or more, e.g., an epimeric purity of at least about 60%, e.g., at least about 70%, 80%, 90%, 95%, 96%, 97%, 98%, 99%, or more, e.g., 99.5% or 99.9% by weight.

In some embodiments, compound 1 (or salt thereof) produced by the methods of the present invention contains less than 20 different measurable impurities, e.g., less than 15 impurities, e.g., less than 15, 14, 13, 12, 11, 10, 9, 8, 7, or 6 impurities, e.g., 5 or less impurities. A measurable impurity, as used herein, refers to an impurity that can be detected by methods routinely used in the art to test chemical purity, e.g., HPLC or mass spectrometry. A measurable impurity is one that is present in an amount greater than 0.03 wt %.

In some embodiments, compound 1 (or salt thereof) produced by the methods of the present invention contains less than about 4.0% by weight of the epimer compound 6, e.g., less than about 3.5%, 3.0%, 2.5%, 2.0%, 1.9%, 1.8%, 1.7%, 1.6%, 1.5%, 1.4%, 1.3%, 1.2%, 1.1%, or 1.0%.

In some embodiments, compound 1 (or salt thereof) produced by the methods of the present invention contains less than about 2.5% by weight of total impurities excluding the epimer compound 6, e.g., less than about 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, or 0.5%.

In some embodiments, compound 1 (or salt thereof) produced by the methods of the present invention contains less than about 1.0% by weight of any individual impurity including the epimer compound 6 or excluding the epimer compound 6, e.g., less than about 1.0%, 0.95%, 0.9%, 0.85%, 0.8%, 0.75%, 0.7%, 0.65%, 0.6%, 0.55%, 0.5%, 0.45%, 0.4%, 0.35%, 0.3%, 0.25%, 0.2%, 0.15%, or 0.1%.

Certain of the compounds described herein contain one or more chiral centers, or may otherwise be capable of existing as multiple stereoisomers. The scope of the present invention includes pure stereoisomers as well as mixtures of stereoisomers, such as purified enantiomers/diastereomers/epimers, enantiomerically/diastereomerically/epimerically enriched mixtures, or racemates. In some embodiments, the compounds have a stereochemical purity of at least about 80%, e.g., at least about 85%, 90%, 95%, 96%, 97%, 98%, 99%, or more.

The compounds of the invention can also exist as tautomeric isomers, e.g., amide/iminol tautomers, in certain cases. Although only one delocalized resonance structure may be depicted, all such forms are contemplated within the scope of the invention.

The compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine. In one embodiment the compounds disclosed herein are prepared in the form of a free base.

It is also understood that the compositions herein comprise compounds and combinations with stoichiometric or non-stoichiometric amounts of water, as in hydrates, or other components, as in solvates.

Synthetic Methods

A further aspect of the invention relates to a method of producing compound 1:

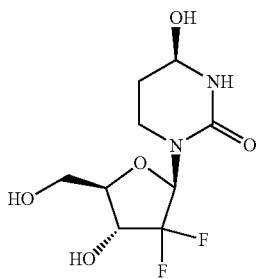

1 or a salt thereof;
comprising precipitating or crystallizing compound 1 from a solution of compound 2:

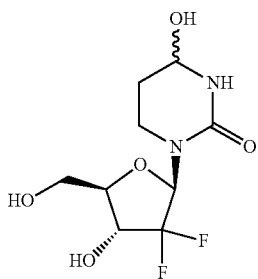

2 in the presence of a catalyst. In one embodiment, the method produces compound 1.

The method takes advantage of crystallization-induced diastereoselective transformation (CIDT) to provide enhanced production of the desired epimer (compound 1). Any suitable catalyst can be used in the method. The term "catalyst" as used herein with respect to the precipitation or crystallization step, refers to a compound that when present in sub-stoichiometric quantities relative to compound 2 promotes equilibration between compound 6 and compound 1. Without being limited by mechanism, it is believed that compound 1 and its epimer compound 6 are in equilibrium with an open aldehyde structure of the compound as an intermediate. The catalyst is thought to act by facilitating the opening of compound 6 to the aldehyde form, thereby increasing conversion of one epimer to the other and equilibrating the amount of compound 1 and compound 6 in solution as, upon usage of an appropriate solvent, compound 1 preferentially precipitates or crystallizes out of solution. The catalyst is present in a catalytically effective amount. In some embodiments, the catalyst can be an acid, e.g., an inorganic acid, e.g., an organic acid, e.g., acetic acid or trifluoroacetic acid. In other embodiments, the catalyst can be a base, e.g., a Bronsted-Lowry base, e.g., a weak base (one that does not ionize fully in an aqueous solution). In other embodiments, the catalyst can be diisopropylethylamine or ammonium hydroxide. In some embodiments, the base has a basicity of 10 or more in a solvent. In some embodiments, the base has a pKa of 10 or more in a solvent, e.g., DMSO, for example as reported in Bordwell, Acc. Chem. Res. 21:456 1988); Crampton, J. Chem. Res. (S) 22 (1997); Kaliurand et al., J. Org. Chem. 65(19):6202 (2000); Kaljurand et al, J. Org. Chem. 70(3):1019 (2005). In some embodiments, the catalyst is a strong base. In some embodiments, the catalyst is a strong base such as a sterically hindered strong base, e.g., a strong base which is a poor nucleophile. In some embodiments, the catalyst is 1,8-diazabicyclo(5.4.0)undec-7-ene (DBU). The DBU may be present in any amount that is effective, e.g., about 1 mol % to about 20 mol %, e.g., about 2 mol % to about 15 mol %, e.g., about 5 mol % to 10 mol %, e.g., about 5 mol %, or e.g., about 10 mol %, e.g., about 1, 2, 3, 4, 5, 6, 7, 8, 9, 10, 11, 12, 13, 14, 15, 16, 17, 18, 19, or 20 mol %. In some embodiments, the DBU may be present at 1 mol % to 20 mol %, e.g., 2 mol % to 15 mol %, e.g., 5 mol % to 10 mol %, e.g., 5 mol %, or e.g., 10 mol %, e.g., 1, 2, 3, 4, 5, 6, 7, 8, 9, 10, 11, 12, 13, 14, 15, 16, 17, 18, 19, or 20 mol %.

Any solvent or combination of solvents can be used that causes preferential precipitation or crystallization of compound 1 over compound 6. In one embodiment, the solvent is a solvent in which compound 6 has greater solubility than compound 1. In some embodiments, the solution used to form the solution of compound 2 comprises, consists essentially of, or consists of an organic solvent. In some embodiments, the solution comprises, consists essentially of, or consists of water or an aqueous solvent. In some embodiments, the solvent is a protic solvent. In some embodiments the solvent is one that is miscible with water. In particular embodiments, the solution is acetonitrile, acetone, tetrahydrofuran, dimethylsulfoxide, or methanol. In particular embodiments, the solution is aqueous acetonitrile, aqueous acetone, aqueous tetrahydrofuran, aqueous dimethylsulfoxide, or aqueous methanol. In a particular embodiment, the solution is aqueous acetonitrile.

The precipitation or crystallization can be carried out for a length of time sufficient for a suitable amount of compound 1 to be formed, e.g., about 0.5 days to 14 days, e.g., about 1-4 days, e.g., about 2-3 days, e.g., about 3-10 days, e.g., about 4-6 days. The precipitation or crystallization can be carried out at any suitable temperature, e.g., at about room temperature, optionally followed by a temperature of about 0° C. to about 10° C. After precipitation or crystallization is complete the precipitate can be collected, e.g., by filtration, and washed, e.g., with aqueous acetonitrile and/or acetonitrile, optionally cooled to a temperature of about 0° C. to about 10° C. The precipitate may then be dried, e.g., under vacuum, e.g., at a temperature lower than about 45° C. The progress of the reaction can be monitored, e.g., by sampling the supernatant of the reaction mixture and determining the ratio of compound 1 to compound 6. Completion of the reaction is indicated by the presence of a 50:50 mixture of compound 1 and compound 6 in the supernatant. If this ratio has not been achieved, additional catalyst can be added and the reaction continued until completion.

Following precipitation or crystallization, compound 1 optionally is further purified by recrystallization or slurrification, e.g., from aqueous acetonitrile, optionally with addition of an acid, e.g., trifluoroacetic acid. For example, the precipitate can be resuspended in water:acetonitrile in a ratio of about 1:2 to about 1:10 (v/v), heated to about 35-45° C., then cooled to about 0° C. The resulting precipitate can be washed in water:acetonitrile in a ratio of about 1:2 to about 1:10 (v/v) and then acetonitrile, optionally cooled to a temperature of about 0° C. to about 10° C. In certain embodiments, compound 1 optionally is further purified by other methods known in the art, such as HPLC.

In some embodiments, compound 1 is further purified by recrystallization in acetone and water, adjusted to a pH of about 6.0 to about 7.4 (e.g., about 6, 6.1, 6.2, 6.3, 6.4, 6.5, 6.6, 6.7, 6.8, 6.9, 7, 7.1, 7.2, 7.3, or 7.4 or any value or range therein), e.g., using aqueous formic acid alone or in combination with aqueous DBU. In some embodiments, the mixture is further heated, e.g., heated to a temperature of about 50° C. to about 55° C., e.g., at a rate of 0.5 to 1.5° C./min until complete dissolution is observed, filtered, washed with a mixture of acetone and water, and then cooled, e.g., cooled to a temperature of about 33° C. to about 43° C., e.g., at a rate of 0.1 to 0.5° C./min, prior to seeding and further cooling, e.g., cooling to a temperature of about −10° C. to about 0° C., e.g., at a rate of 0.1 to 0.5° C./min, and resting, followed by further preparation as known in the art (e.g., filtering, washing, and drying). In some embodiments, the recrystallization mixture is further heated to about 53° C., clear filtered and then cooled to a temperature of about 35° C., seeded, cooled to a temperature of about −5° C., and rested (e.g., aged) for about 12 to about 16 hours (e.g., about 12, 13, 14, 15, or 16 hours or any value or range therein). It has been found by the inventors of the present invention that particular recrystallization parameters as disclosed herein, e.g., higher temperature and/or particular range of pH, generate higher purity product, improve particle size distribution, and avoid dimerization impurities. In some embodiments, the present methods produce a compound having a more uniform particle size distribution, e.g., a unimodal particle size distribution, e.g., a particle size distribution centered around 100-200 μm, e.g., around 130 μm. In some embodiments, at least 50% of the particles have a size between 20 μm and 300 μm, e.g., at least 60%, 70%, 80%, or 90%.

The molar ratio of compound 1 (i.e., the desired epimer) to an epimer of compound 1 (e.g., compound 6) after precipitation or crystallization can be at least about 60:40, e.g., at least about 70:30, 80:20, 90:10, 95:5, or 98:2 or more. The molar ratio of the desired epimer (compound 1) to the other epimer (compound 6) after a second purification step (e.g., recrystallization or slurrification) can be at least about 80:20, e.g., at least about 90:10, 95:5, or 98:2 or more.

Another aspect of the invention relates to a method of producing compound 1:

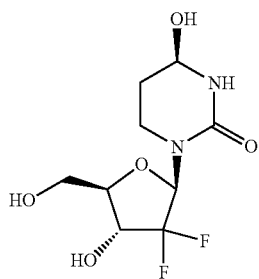

or a salt thereof;
comprising the steps of:
(a) hydrogenating the starting compound of Formula IV:

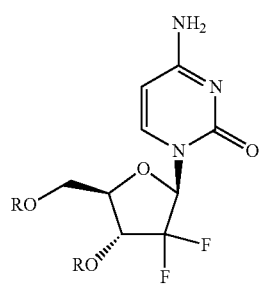

wherein R is a hydroxyl protecting group,
to produce the compound of Formula IIa:

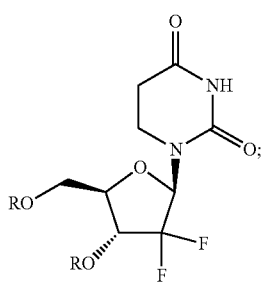

(b) reducing the compound of Formula IIa to produce the compound of Formula IIIa:

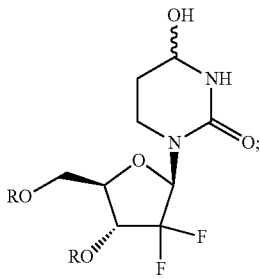

(c) deprotecting the compound of Formula IIIa to produce compound 2:

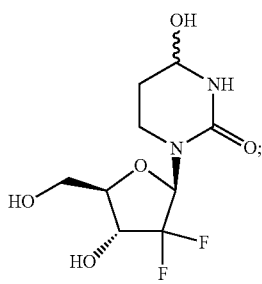

and
(d) precipitating or crystallizing compound 2 in the presence of a catalyst to produce compound 1:

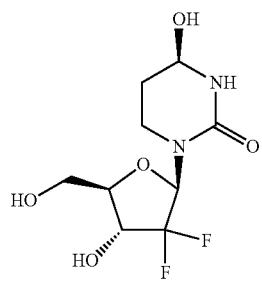

or a salt thereof;
wherein the method comprises one or more of the following in any combination:
(i) wherein the hydrogenating step (a) is performed under hydrogen atmosphere with a palladium catalyst;
(ii) wherein the reducing step (b) is performed at a temperature of about −12° C. to about −5° C.;
(iii) wherein the deprotecting step (c) is performed in the presence of an organic base; and/or
(iv) wherein the work-up of the deprotected compound from deprotecting step (c) is performed under non-aqueous conditions. In some embodiments, the present invention further comprises a step wherein the final product is recrystallized and the recrystallizing is performed at a pH of about 6.0 to about 7.4 and carried out by dissolving the final product at a temperature of about 50° C. to about 55° C. to produce a solution and then cooling the solution to about 5° C.

The starting compound of Formula IV can be obtained commercially, e.g., from Aurora Fine Chemicals (San Diego, CA), or synthesized by known methods, for example as disclosed in Wheeler et al., J. Labeled Compounds Radiopharm. 29:583 (1991) and Chou et al., Synthesis 6:565 (1992), incorporated by reference herein in their entirety.

The hydrogenation of the compound of Formula IV in step (a) to produce the compound of Formula IIa can be carried out by methods known in the art, e.g., as disclosed in U.S. Pat. No. 8,268,800 and/or Patent Publication WO 2015/066162, the disclosures of which are incorporated herein by reference in their entirety. For example, the step can be carried out under catalytic transfer hydrogenation conditions, e.g., in the presence of palladium on charcoal (Pd/C), e.g., in the presence of about 5% Pd/C. The amount of catalyst, e.g., Pd/C, used in the hydrogenating step (a) may be any catalytic effective amount, e.g., a catalytic amount of not more than 0.1 part by weight per one part by weight of a compound of Formula IV. In some embodiments, the amount of Pd/C used in hydrogenating step (a) may be, for example, about 0.025 to about 0.05 parts Pd/C per one part by weight of a compound of Formula IV. The hydrogenation may occur by heating the compound of Formula IV to reflux, e.g., with formic acid and hydrochloric acid or with hydrogen (e.g., at about 2 to about 4 bar hydrogen pressure) and optionally with acetic acid) in a solvent, e.g., aqueous ethyl acetate. Hydrogenation may be carried out at a temperature of about 0° C. to about 100° C., e.g., about 50° C. to about 80° C., e.g., about 63° C. to about 77° C., e.g., at about 68° C. for about 0.5-48 hours, e.g., about 5 to about 24 hours, about 10 to about 20 hours, about 15 to about 20 hours, or any value or range therein, e.g., about 24 hours. The reagents used to affect hydrogenation (e.g., palladium and charcoal) may be added after the reaction mixture is brought to the elevated temperature (e.g., about 50° C. to about 80° C., or, at about 68° C.). After completion, the catalyst may be removed, e.g., by filtering, e.g., at about 60° C. to about 70° C., and washed, e.g., with ethyl acetate. After separation of the organic layer it may be washed, e.g., with aqueous potassium carbonate, aqueous sodium bicarbonate, and/or aqueous NaCl. The organic layer may be reduced in volume (e.g., by distillation), and the residue heated (e.g., at about 70° C.) until dissolution and cooled (e.g., to about 45° C. to about 55° C.), seeded with product and stirred, e.g., for about 1 h, e.g., at about 45° C. to about 55° C. The reaction mixture may be reduced in volume (e.g., by distillation), and methyl tert-butyl ether slowly added at a temperature of about 40° C. to about 50° C., then the reaction mixture slowly cooled to about 0° C. to about 10° C. The resulting suspension may be stirred, e.g., for about 2 to about 16 h and then filtered. The filtrate may be washed, e.g., with methyl tert-butyl ether, optionally cooled to about 0° C. to about 10° C.

Alternatively, the filtrate from the hydrogenation reaction may be washed (e.g., with acetic acid), heated (e.g., to about 80° C.) to be dissolved and water (e.g., preheated to about 80° C.) added. After cooling, the precipitate may be collected by filtration, washed (e.g., with water and ethanol), and dried.

The solvent used in hydrogenating step (a) herein may be any conventional solvent which does not cause adverse effects in the reaction. Non-limiting examples of such solvents for hydrogenation include, water, alcohols (e.g., methanol, ethanol, isopropanol, n-butanol, trifluoroethanol, ethylene glycol), ethers (e.g., tetrahydrofuran, dioxane, diethyl ether, diglyme), esters (e.g., methyl acetate, ethyl acetate), other organic solvents, and/or a mixed solvent of two or more solvents as disclosed herein. The reaction may be preferably performed in the presence of an organic acid such as formic acid, acetic acid, oxalic acid, maleic acid, fumaric acid, malic acid, tartaric acid, citric acid, succinic acid, and/or benzoic acid. In some embodiments, hydrogenation may be performed in a mixed solvent comprising ethyl acetate, acetic acid, and water.

In some embodiments, the hydrogenation may be performed under increased pressure (relative to ambient pressure), e.g., increased pressure of about 0.1 to about 1 megapascal (MPa), e.g., about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 0.96, 0.97, 0.98, 0.99, or 1 MPa or any value or range therein. In some embodiments, the hydrogenating step (a) may be performed under ambient (e.g., ordinary, e.g., normal) pressure. In some embodiments, the hydrogenating step (a) may be performed under increased pressure of about 0.1 to about 0.85 MPa, or about 0.15 to about 0.73 MPa, or about 0.1 to about 0.5 MPa.

The reduction of the compound of Formula IIa to the compound of Formula IIIa in step (b) can be carried out by methods known in the art, e.g., as disclosed in U.S. Pat. No. 8,268,800 and/or Patent Publication WO 2015/066162. For example, reduction may be carried out with a reducing agent such a sodium borohydride in an organic solvent, e.g., a mixture of methylene chloride and ethanol. The reduction can be carried out at any suitable temperature, e.g., around −5° C. to about 10° C., e.g., about 0° C. to about 5° C., for about 0.5 to 3 hours, e.g., about 1.5 hours.

In some embodiments, the reduction may be carried out at a temperature of about −12° C. to about −3° C., e.g. about −12, −11, −10, −9, −8, −7, −6, −5, −4, or −3° C. or any value or range therein. In some embodiments, the reduction may be carried out at a temperature of about −11° C. to about −3° C., about −12° C. to about −5° C., about −11° C. to about −5° C., or about −10 to about −6° C., or at a temperature of about −8° C. This invention is based, in part, on the surprising discovery that unusually cold conditions (e.g., a temperature of about −11° C. to about −5° C.) minimizes formation of impurities such as, but not limited to, DPU and DCU and indirectly CYU (which is produced by conversion of DCU in the subsequent step), which does not purge well further in production of compound 1. Structures of exemplary impurities are shown in Table 1.

TABLE 1

Reduction Impurity Examples (Bz = benzoyl)

| Impurity | Structure |
|---|---|
| DPU | 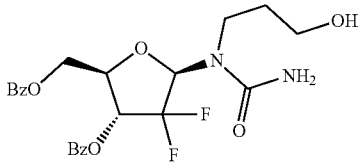 |
| DCU | 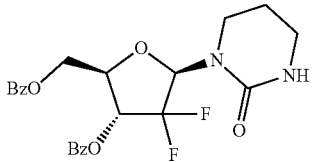 |

TABLE 1-continued

Reduction Impurity Examples (Bz = benzoyl)

| Impurity | Structure |
|---|---|
| CYU | 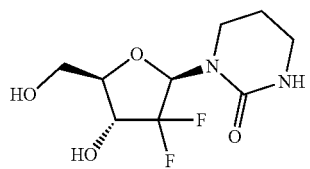 [SMILES: O=C1NCCCN1[C@@H]1O[C@H](CO)[C@@H](O)C1(F)F] |

The reduction may optionally be carried out in the presence of cerium trichloride. In one embodiment, the amount of cerium chloride is about 50 mol % (e.g., 50 mol %). In another embodiment, the amount of cerium chloride is about 20 mol % or about 10 mol % (for example 20 mol % or 10 mol %). Following addition of cerium (III) chloride the reaction may be heated (e.g., to about 15° C. to about 25° C.), e.g., for about 20 minutes, before cooling.

Following the reduction, the reaction can be quenched, e.g., with acetone, and the solution neutralized with an acid, e.g., citric acid. The organic layer containing the compound of Formula IIIa can be separated and washed, e.g., with water. The organic layer may be heated (e.g., to about 20° C. to about 30° C.) and the pH adjusted with acid (e.g., citric acid), with thus step being repeated until the pH is stable. The organic phase may be washed (e.g., with sodium bicarbonate), e.g., at a temperature of about 20° C. to about 35° C., and then with water, at a temperature of about 0° C. to about 10° C. The organic phase may be reduced in volume (e.g., by distillation), methyl tert-butyl ether may be added and the resulting precipitant collected, washed with methyl tert-butyl ether cooled to about 0° C. to about 10° C., and dried.

The deprotection of the compound of Formula IIIA to produce compound 2 in step (c) may be carried out by methods known in the art, e.g., as disclosed in U.S. Pat. No. 8,268,800 and/or Patent Publication WO 2015/066162. For example, deprotection can be carried out in the presence of a weak base, e.g., ammonium hydroxide, in a solvent, e.g., methanol. In some embodiments, deprotection may be carried out in the presence of an organic base, e.g., one or more bases selected from the group consisting of DBU, trimethylamine, N,N-dimethyl-4-aminopyridine (DMAP), and 1,3-diazabicyclo[2.2.2]octane (DABCO). In some embodiments, deprotection may be carried out in the presence of ammonia, in a solvent, e.g., methanol, e.g., at a temperature of about 20° C. to about 30° C. The amount of organic base used in deprotecting should not be limited as long as it is a requisite amount and does not cause any adverse effect, e.g., does not cause side-reaction. In some embodiments, the amount of organic base used in deprotecting may be about 0.01 to about 2.2 moles per mole of a compound of Formula IIIa (e.g., about 0.01, 0.02, 0.03, 0.04, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.15, 2.16, 2.17, 2.18, 2.19, or 2.2 moles per mole of a compound of Formula IIIa or any value or range therein). For example, in some embodiments, the deprotecting step (c) may be performed in the presence of about 0.01 to about 2.2 moles of an organic base per mole of a compound of Formula IIIa, or about 0.05 to about 2.0 moles of an organic base per mole of a compound of Formula IIIa, or about 1.0 to about 1.9 moles of an organic base per mole of a compound of Formula IIIa. The deprotection may be carried out for about 12-48 hours, e.g., about 24 hours.

Following deprotection, the mixture may be concentrated, dissolved in an aqueous solvent, e.g., water, and washed with an organic solvent, e.g., ethyl acetate.

In some embodiments, after deprotection the work-up may be performed under non-aqueous conditions, e.g., with an evaporative solvent exchange process. The inventors of the present invention discovered that use of a non-aqueous evaporative solvent exchange process forms a non-sticky solid and avoids hydrolytic instability and dimer formation. In some embodiments, deprotection may be further followed by additional trituration to remove impurities, e.g., genotoxic impurities such as, but not limited to, benzamide. In some embodiments, deprotection in a non-aqueous work-up may be performed with isopropanol and/or with acetonitrile.

In some embodiments, a non-aqueous work-up may be performed by reducing the volume of the reaction mixture (e.g., by distillation under reduced pressure), adding methanol and continuing to reduce volume, adding isopropanol and acetonitrile and continuing to reduce volume, then adding acetonitrile and continuing to reduce volume. The reaction may then be cooled, e.g., to about 0° C. to about 10° C., e.g., over 1-2 hours and maintained, e.g., for 1-6 hours. The solid product may be collected and washed with acetonitrile.

The precipitation or crystallization of compound 2 to produce compound 1 in step (d) may be carried out as described above.

In some embodiments, the precipitation or crystallization of compound 2 at step (d) to produce compound 1 may proceed by suspending the compound in the presence of DBU, acetic acid, trifluoroacetic acid, diisopropylethylamine, and/or ammonium hydroxide, optionally under cooling.

In some embodiments, a method of the present invention may comprise the steps of (a) through (d), wherein the reducing step (b) is performed at a temperature of about −12° C. to about −3° C., thereby minimizing formation of DCU and DPU and indirectly CYU. CYU does not purge well from rest of synthesis. In some embodiments, a method of the present invention may further comprise performing the work-up of the deprotected compound from the deprotecting step (c) under non-aqueous conditions (e.g., evaporative solvent exchange, thereby generating a non-sticky solid and/or avoiding hydrolytic instability and/or dimer formation. In some embodiments, a method of the present invention may further comprise wherein the deprotecting step (c) further comprises a step of trituration, thereby removing genotoxic impurities e.g., benzamide. In some embodiments, a method of the present invention may further comprise recrystallizing the final product, wherein the recrystallization is performed at a pH of about 6.0 to about 7.4 and at a temperature of about 50° C. to about 55° C.

In some embodiments, a method of the present invention may comprise the steps of (a) through (d), wherein the hydrogenating step (a) is performed under hydrogen atmosphere with a palladium catalyst, and/or wherein the deprotecting step (c) is performed in the presence of an organic base. Specifically, with regard to step (a), WO 2015/066162 has succeeded in high-yield hydrogenation by protecting the hydroxyl groups and then by carrying out the hydrogenating step with large amounts of formic acid in the presence of considerable Pd/C as an improved method of the disclosures of U.S. Pat. No. 8,268,800, but the improved step from WO 2015/066162 still had other disadvantages from the viewpoint of industrial production, e.g., expensive Pd/C is used in large amounts, and formic acid which is not suitable as reagent in industrial production is used in large amounts. The present invention has made it possible to carry out the hydrogenating step in high yield and high purity by performing the hydrogenating step (a) under hydrogen atmosphere in the presence of a catalytic amount of palladium catalyst. In addition, the deprotecting reaction in WO 2015/066162 needs to be performed with ammonia over extended time, which is troublesome for industry-scale production and generates hard-to-remove impurities. As compared to U.S. Pat. No. 8,268,800, the hydrogenating step was carried out with hydroxyl groups that were not protected, in the presence of large amounts of expensive rhodium catalyst, leading to, e.g., high manufacturing cost, low purity of product, and difficult purification by chromatography. The problems of WO 2015/066162 and U.S. Pat. No. 8,268,800 noted above are overcome by the invention as disclosed herein.

Uses

Compound 1 or a pharmaceutically acceptable salt thereof produced by the present invention can be used to inhibit CDA activity. Compound 1 or a pharmaceutically acceptable salt thereof can be in the form of a pharmaceutical composition, e.g., together with a pharmaceutically acceptable excipient. In some embodiments, compound 1 or a pharmaceutically acceptable salt thereof may be used in a method for treating cancer in a subject in need thereof in combination with a CDA substrate drug, e.g., a CDA substrate drug that may be used to treat cancer. Examples of CDA substrate drugs include, without limitation, decitabine, 5-azacytidine, gemcitabine, ara-C, tezacitabine, 5-fluoro-2'-deoxycytidine, and cytochlor. In some embodiments, the cancer may be selected from the group consisting of hematological cancers and solid cancers. In certain embodiments, the hematological cancer may be myelodysplastic syndromes or leukemia, e.g., acute myeloid leukemia or chronic myeloid leukemia. In certain embodiments, the solid cancer may be pancreatic cancer, ovarian cancer, peritoneal cancer, non-small cell lung cancer, metastatic breast cancer, bladder cancer, squamous cell carcinoma, transitional cell carcinoma, adenocarcinoma, gynecological cancer, fallopian tube carcinoma, liver cancer, hepatocellular carcinoma, lung cancer, cervical carcinoma, genitourinary tract cancer, or gastrointestinal cancer. In some embodiments, compound 1 or a pharmaceutically acceptable salt thereof may be administered at substantially the same time with the CDA substrate drug, prior to the CDA substrate drug or after the CDA substrate drug, optionally in a single unit dosage form or in multiple, separate unit dosage forms. Embodiments according to the present invention are described in non-limiting examples below.

EXAMPLES

Example 1. Hydrogenation Step (a)

The hydrogenation of the compound of Formula IV (1 equiv.) in step (a) to produce the compound of Formula IIa was carried out with hydrogen at 2 to 4 bar hydrogen pressure and acetic acid (80%, 2.62 g/g) in ethyl acetate (8.97 g/g) in the presence of Pd/C (5%, 0.05 g/g) in water (1.98 g/g) at a temperature of 63° C. to 77° C. for at least 12 hours. After completion, the catalyst was removed by filtering, and the filter cake washed with ethyl acetate (6.73 g/g). After cooling, the filtrate was washed with aqueous potassium carbonate. The organic phase was washed with aqueous sodium bicarbonate (7% w/w, 5.38 g/g), and washed with aqueous NaCl (10% w/w, 3 g/g). The organic layer was distilled to a residual volume of ca. 8 volumes, and the residue heated to 70° C. until dissolution and cooled to 45° C. to 55° C. The reaction was seeded with the compound of Formula IIa, and the reaction mixture was distilled to a residual volume of ca. 2 volumes, and methyl tert-butyl ether (4.44 g/g) slowly added at a temperature of 40° C. to 50° C. After cooling the mixture, the precipitated crystal was collected on a filter, washed with methyl tert-butyl ether (1.48 g/g) cooled to 0° C. to 10° C. and the product dried to give Formula IIa. Yield: 86%. Chemical purity: 98.9%.

Example 2. Reducing Impurities During Reduction Step (b)

The compound of Formula IIa (1 equiv.) was dissolved in dichloromethane (14.6 g/g) and stirring. Ethanol (5.83 g/g) was added, and the reaction mixture cooled to −5° C. to 5° C. Cerium(III) chloride heptahydrate (0.08 g/g) was added, and the reaction heated to 15° C. to 25° C. Water (0.68 g/g) was then added, and the reaction stirred for a least 20 min before cooling to 0° C. to −11° C. Sodium borohydride (0.11 g/g) was added portion-wise, maintaining the temperature between 0° C. to −11° C. and the reaction stirred until completion. Acetone (0.73 g/g) was added, maintaining the temperature between 0° C. to −11° C. An aqueous solution of citric acid (3.7 to 4.4% w/w) was slowly added until a pH of 6.5 to 7.5 was achieved. The phases were allowed to settle and the aqueous phase was separated. The organic phase was washed with an aqueous solution of sodium bicarbonate and then further washed with water. The phases were separated and the organic phase was further washed with water. The organic phase was distilled under vacuum at ≤35° C. until a volume of ca. 2 volumes, then methyl tert-butyl ether (7.38 g/g) was added and distilled under vacuum at ≤35° C. until a volume of 4.8 volumes. A second portion of methyl tert-butyl ether (3.7 g/g) was added and distilled under vacuum at ≤30° C. until a volume of 4.8 volumes. Further methyl tert-butyl ether (2.67 g/g) was added and the reaction mixture cooled to 0° C. to 10° C. in ≥4 h. Further methyl tert-butyl ether (0.89 g/g) was added and the reaction mixture was stirred at this temperature and then the solid product isolated and washed with methyl tert-butyl ether (1.46 g/g) pre-cooled to 0° C. to 10° C., and the product dried to give Formula IIIa. Yield: 76%. Chemical purity: 93%.

The processes of Entries 1-5 were carried out in a similar manner to above except changing the temperature of reduction to 0° C., −3° C., −5° C., −8° C., and −11° C., respectively. Lower temperatures minimized formation of DCU, DPU, and CYU as shown in Table 2. Structures of impurities are shown in Table 1.

TABLE 2

| Entry No. | Temperature of Reduction | DPU (% Area) in Compound of Formula IIIa (step b) | DCU (% Area) in Compound of Formula IIIa (step b) | CYU (% area) in Compound 1 | Yield Step b |
|---|---|---|---|---|---|
| 1 | 0° C. | 2.42 | 0.69 | 0.08 | 73.6% |
| 2 | −3° C. | 1.91 | 0.25 | 0.03 | 69.8% |
| 3 | −5° C. | 2.18 | 0.15 | ND | 77.2% |
| 4 | −8° C. | 0.7 | 0.10 | ND | 81.8% |
| 5 | −11° C. | 0.40 | <0.05 | Not carried forward | 83.5% |

Example 3. Improvements During Deprotecting Step (c)

Deprotection was carried out in a solution of ammonia (0.87 g/g) in methanol (4.95 g/g). The compound of Formula IIIa (1 equiv.) and further methanol (1.58 kg/kg) was added. The reaction mixture was adjusted to 20° C. to 30° C. and stirred at this temperature until completion. The work-up was performed by distilling the reaction mixture under reduced pressure until a residual volume of ca. 3 volumes. Methanol (1.58 g/g) is added and distillation continued under reduced pressure until a residual volume of ca. 3 volumes. Isopropanol (1.92 g/g) was added followed by acetonitrile (3.93 g/g) and distillation was continued under reduced pressure until a residual volume of approximately 3 volumes. Acetonitrile (5.51 g/g) was added and distilled under reduced pressure until a residual volume of 5 volumes was reached. Further acetonitrile (1.58 g/g) was added and distilled under reduced pressure until a residual volume of ca. 5 volumes was reached. After cooling the mixture, the solid product was isolated and washed with acetonitrile (1.56 g/g) pre-cooled to 0° C. to 10° C. The wet product was mixed with acetonitrile (2.37 g/g). After cooling the mixture, the wet product was then dried to give Compound 2. Yield: 87%. Chemical purity: 97%.

Reference Example 4. Original Deprotection Step (c)

Deprotection was performed by treating with ammonia (7.0 M in methanol, 25 equiv). The mixture was stirred at 25° C. for 27 h and then concentrated under reduced pressure. The residue was dissolved in water (6.3 volumes) and washed twice with ethyl acetate (5.7 volumes each). The aqueous layer was concentrated under reduced pressure at a temperature less than 35° C. to give compound 2 (95% yield).

When continued forward using the typical process conditions, compound 2 generated from the original deprotection conditions typically afforded Compound 1 with generally lower overall purity and a significantly higher number of impurities. See Table 3, Entries 1 and 2.

Example 5. Highly Specific Crystallization Conditions with High Temperatures

Conditions for crystallization of Compound 1 for improved purity were tested. Highly specific crystallization conditions were found to generate very pure material, improve control of particle size distribution to within optimal (unimodal) range, lower levels of acetonitrile, and avoid dimerization impurities. Specific conditions include higher temperatures used and adjustment to pH.

Preferred steps for recrystallization of Compound 1 were performed by mixing Compound 2 (1 equiv.), 1,8-diazabicyclo[5,4,0]undec-7-ene (DBU, 0.028 g/g), acetonitrile (5.02 g/g) and water (0.73 g/g) and stirring at 15° C. to 25° C. for 2 h. The mixture was cooled to 0° C. to 10° C. in ≥1 h and maintained at this temperature for 1 to 8 h. The solid product was collected by filtration and washed with acetonitrile:water (0.21 g/g:0.033 g/g) cooled to 0° C. to 10° C. The wet product and acetonitrile (2.36 g/g) were stirred at 0° C. to 10° C. for 30 min to 8 h. The solid product was collected and washed with acetonitrile (0.78 g/g) cooled to 0° C. to 10° C. The wet product was dried to give Crude Compound 1. Yield: 80%. Chemical purity: 94%.

Crude Compound 1 (1 equiv.), acetone (6.26 g/g) and water (2 g/g) were mixed at a temperature of 20° C. to 30° C. The pH of the reaction mixture was adjusted to 6.0 to 7.5 with an aqueous solution of formic acid (0.0076 g/g formic acid in 1.25 g/g water). If required, an aqueous solution of 1,8-diazabicyclo[5,4,0]undec-7-ene DBU (0.041 g/g DBU in 0.78 g/g water) can be used to adjust the pH to the target range. The reaction mixture was heated to 50° C. to 55° C. until complete dissolution was observed and filtered into a reactor set to 40° C. to 50° C. and washed with a mixture of water (0.1 g/g) and acetone (0.31 g/g). The solution was cooled to 33° C. to 43° C. and seeded with 0.005 g/g of Compound 1. The reaction was maintained at this temperature before cooling to −10° C. to 0° C. The suspension was maintained at −10° C. to 0° C. for 12 to 16 h and isolated by filtration. The product was washed with acetone (0.78 g/g) and dried to give Compound 1. Yield: 61%. Chemical purity excluding epimer: 99.6%. Compound 6 of the following formula which is an epimer of Compound 1 was produced in the following ratio. Compound 1: Compound 6=99.6:0.4. (PSD: D(0.9)=252 μm, D(0.5)=125 μm, D(0.1)=21 μm).

Example 6. Comparison to Original Purification Process

Crude compound 1 (1 equiv.) was suspended in a mixture of acetone (2.5 ml/g) and water (2.5 ml/g) and stirred at 25±2° C. for 2 hours. The mixture was cooled to 5±2° C. and stirred for 2 hours and then filtered. The filter cake was rinsed with acetone (2×0.55 ml/g) and then dried under vacuum at 55° C. Compound 1 was afforded in 67% yield. Chemical purity excluding epimer: 99.4%. Compound 6 of the following formula which is an epimer of Compound 1 was produced in the following ratio. Compound 1: Compound 6=98.7:1.3.

Overall purity and ratio of compound 1 to compound 6 is lower in the original process compared to the updated purification process. The impurity profile is shown in Table 3. Structures of monitored impurities are shown in Table 4.

TABLE 3

|  | Entry 1 Original Process | Entry 2 Improved Process |
|---|---|---|
| Related Substances - HPLC - specified (% by weight) Compound 6 (Epimer) | 1.34 | 0.62 |
| NHD-1 | 0.05 | 0.07 |
| NHD-2 | 0.04 | 0.07 |
| HTD-1 | 0.1 | ND |
| HHD-1 | 0.07 | ND |
| HTD-2 | 0.03 | ND |
| MPO-1 | 0.11 | 0.06 |
| RRT 0.62 | 0.06 | 0.23 |
| RRT 0.92 | ND | 0.05 |
| RRT 3.09 | 0.05 | ND |
| RRT 5.98 | 0.04 | ND |
| RRT 6.34 | 0.06 | ND |
| RRT 6.38 | 0.07 | ND |
| RRT 6.43 | 0.04 | ND |
| RRT 6.98 | 0.05 | ND |
| RRT 7.56 | 0.03 | ND |
| Total excluding epimer (%) | 0.6 | 0.5 |
| Total # excluding epimer | 14 | 5 |

ND = not detected.

TABLE 4

| Impurity | Structure |
|---|---|
| NHD-1/NHD-2 | 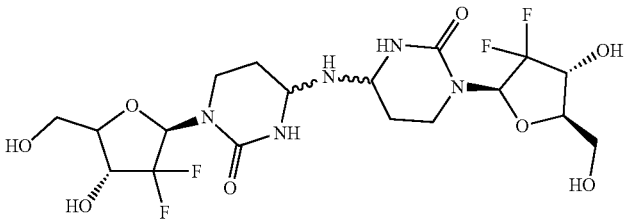 |
| HTD-1/HTD-2 | 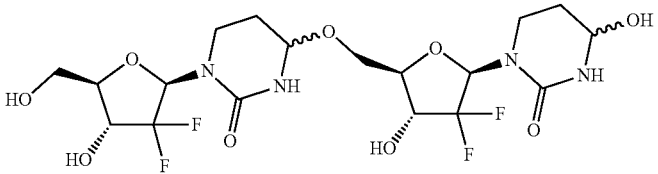 [SMILES: O=C1NC(O)CCN1[C@@H]1O[C@H](COC2CCN([C@@H]3O[C@H](CO)[C@@H](O)C3(F)F)C(=O)N2)[C@@H](O)C1(F)F] |
| HHD-1 | 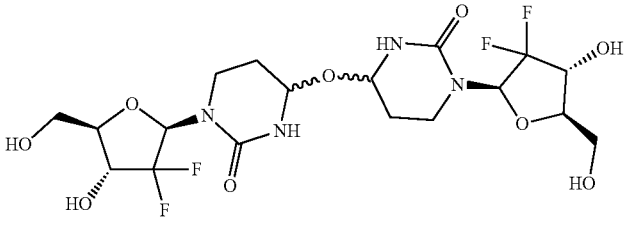 |
| MPO-1 | 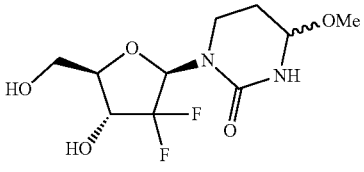 [SMILES: COC1CCN([C@@H]2O[C@H](CO)[C@@H](O)C2(F)F)C(=O)N1] |

Example 7. Alternative Methods for Step (a) and (c)

Step (a)

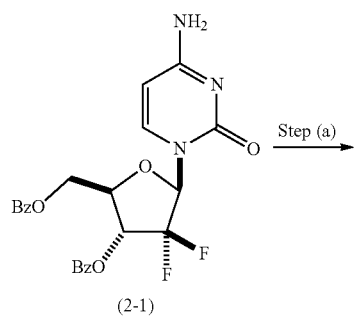

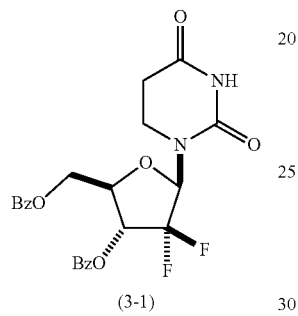

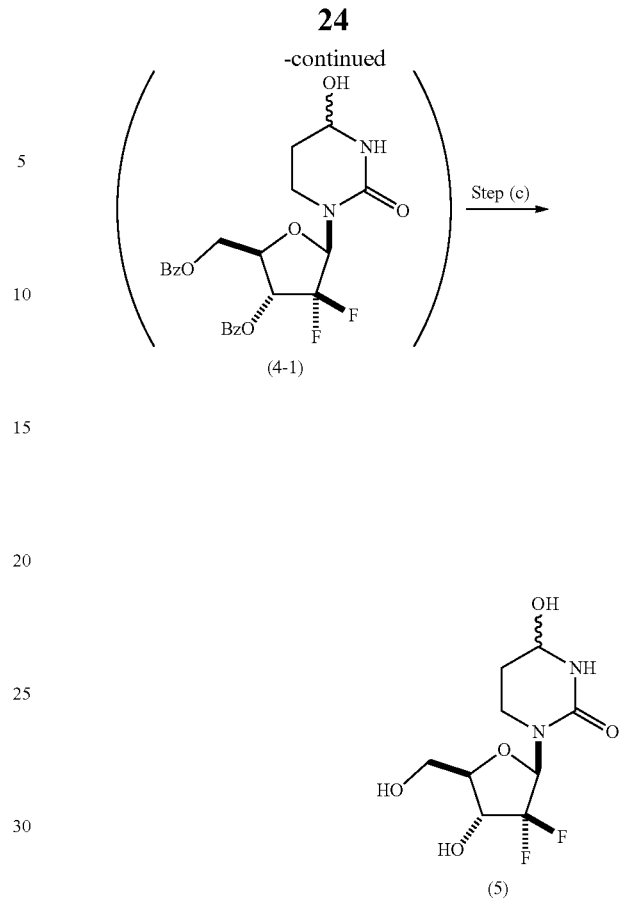

A mixture of Compound (2-1) (20.0 g, 42.4 mmol), ethyl acetate (200 mL), acetic acid (80 mL), and water (50 mL) was dissolved with stirring at 50 to 60° C. under nitrogen atmosphere, and then 0.2 g of Pd/C (10% by weight, 5 wt % by dry basis, 50% water wet, NEs-5DR type) was added thereto and the atmosphere in the reaction vessel was replaced with nitrogen. Subsequently, the atmosphere was replaced with hydrogen, and the reaction mixture was stirred under increased pressure of hydrogen (0.5 MPa) at 50 to 60° C. for 18 hours. The reaction mixture was filtrated and the residue on the filter was washed with 20 mL of 80% acetic acid. The ethyl acetate in the filtrate was removed in vacuo (100 Torr, 50° C.). The residual solution was heated at 80° C. to be dissolved, and 400 mL of water heated beforehand at 80° C. was added thereto. After cooling the mixture, the precipitated crystal was collected on a filter, washed with water and ethanol, and dried to give 19.24 g of Compound (3-1) (yield: 95.6%, chemical purity: 98.4%).

Steps (b) and (c)

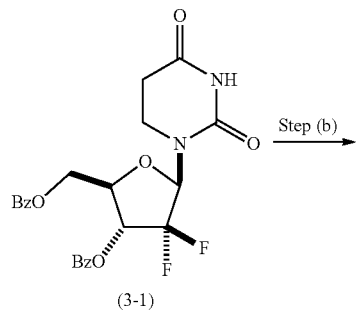

Synthesis of Compound (4-1): Compound (3-1) (19.0 g, 40.0 mmol) was dissolved in methylene chloride (228 mL) with stirring. To the solution were added ethanol (152 mL) and cerium (III) chloride heptahydrate (1.49 g, 4.0 mmol), and the mixture was cooled to a temperature below 6° C. A solution of sodium borohydride (3.77 g, 100 mmol) in water (19 mL) was added dropwise to the cooled mixture while keeping the temperature thereof below 6° C. After the addition, the reaction mixture was reacted at a temperature below 6° C. for 2 hours. Keeping the temperature of the reaction mixture below 6° C., the reaction mixture with stirring was quenched with 9.5 mL of acetone, and then 114 mL of 0.5 M aqueous hydrochloric acid was added thereto, while keeping the temperature thereof below 6° C., to adjust the quenched mixture to pH 7. After warming the mixture to 30 to 40° C., 114 mL of aqueous saturated sodium bicarbonate was added to the mixture. The mixture was separated with a separating funnel, the organic layer was washed with 114 mL of water, and the solvent was removed in vacuo (50 Torr, 40° C.). The obtained Compound (4-1) was used at the next step without purification.

Synthesis of Compound 5: To Compound (4-1) obtained at Step (b) were added methanol (190 mL) and 1,8-diazabicyclo[5.4.0]undec-7-ene (DBU) (0.30 mL, 2.0 mmol), and the reaction mixture was warmed to 40° C. and stirred at 40° C. for 3 hours. After the reaction, the methanol was removed in vacuo (50 Torr, 40° C.), and 95 mL of acetonitrile was added to the residual solution. After cooling, the precipitated crystal was collected on a filter, washed with cooled acetonitrile, and dried to give 8.96 g of Compound 5 (yield: 83.4%, chemical purity: 97.1%).

Step (d)

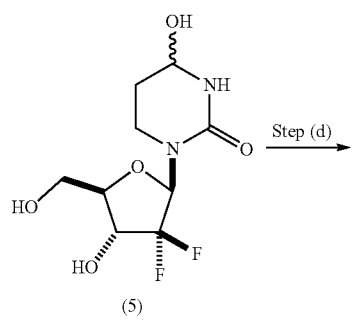

Step (d) →

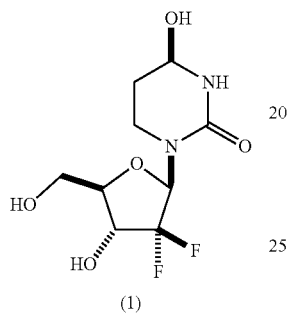

Synthesis of crude Compound (1): A mixture of Compound (5) (0.9 g, 3.35 mmol), acetonitrile (5.8 mL), water (0.65 mL) and 1,8-diazabicyclo[5.4.0]undec-7-ene (DBU) (0.025 mL, 0.17 mmol) was suspended, and the suspension was continued to be stirred for 48 hours at 20 to 30° C. After cooled, the precipitated crystal was collected on a filter, washed with cooled 90% acetonitrile and acetonitrile, and dried to give 0.66 g of Compound 1 (yield: 73.0%, chemical purity: 98.3%). Compound 5: Compound 6 (epimer of Compound 5)=98.9:1.1.

Purification of crude Compound 1: Compound 1 (0.3 g, 1.11 mmol) was suspended in a mixture of acetonitrile (0.96 mL) and water (0.24 mL), and the suspension was stirred for two hours with warming at 40 to 50° C. Then, the suspension was stirred for two hours at a temperature below 5° C. The obtained precipitate was collected on a filter, washed with cooled 90% acetonitrile and acetonitrile, and dried to give 0.66 g of Compound 1 (yield: 73.5%, chemical purity: 99.6%). Compound 6 of the following formula which is an epimer of Compound 1 was produced in the following ratio. Compound 1: Compound 6=99.7:0.3.

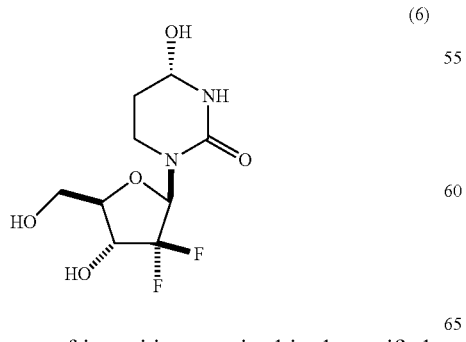

The total amount of impurities contained in the purified Compound 1 was 0.46% by area percentage. Separately, Compound 1 was prepared from the same materials and purified, by the method disclosed in Patent Literature 2 (WO 2015/066162), but the total amount of impurities therein was higher (2.46%) than that of the above-mentioned process, which means that the process of the present invention can provide a method to prepare Compound 1 in higher yield.

EMBODIMENTS

Embodiments of the invention include, without limitation, the following.

1. A method of producing compound 1:

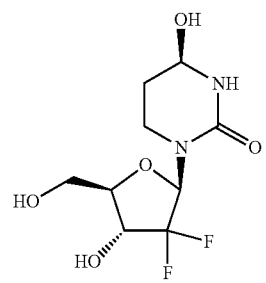

or a salt thereof;
comprising the steps of:
(a) hydrogenating a compound of Formula IV:

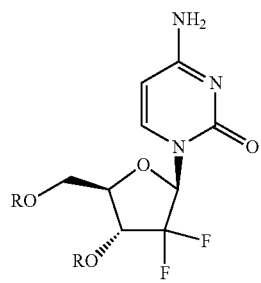

wherein R is a hydroxyl protecting group,
to produce a compound of Formula IIa:

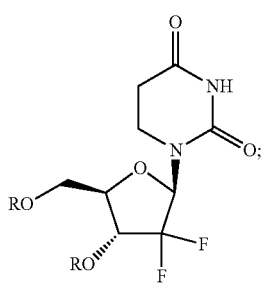

(b) reducing the compound of Formula IIa to produce a compound of Formula IIIa:

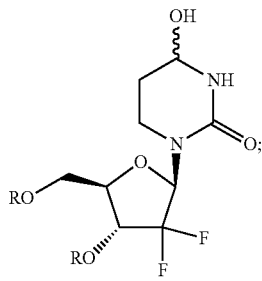

(c) deprotecting the compound of Formula IIIa to produce compound 2:

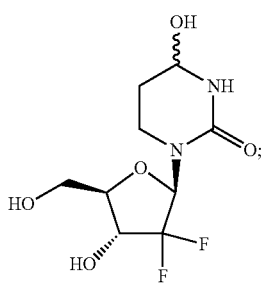

and
(d) precipitating or crystallizing compound 2 in the presence of a catalyst to produce compound 1:

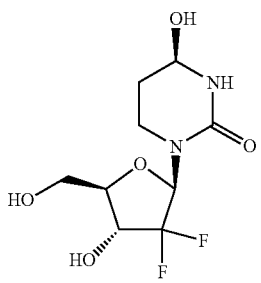

or a salt thereof;
wherein the method comprises one or more of the following in any combination:
  (i) wherein the hydrogenating step (a) is performed under hydrogen atmosphere with a palladium catalyst;
  (ii) wherein the reducing step (b) is performed at a temperature of about −12° C. to about −5° C.;
  (iii) wherein the deprotecting step (c) is performed in the presence of an organic base; and/or
  (iv) wherein the deprotecting step (c) is performed under non-aqueous conditions.

2. The method of embodiment 1, wherein the catalyst is about 1 mol % to about 20 mol % DBU.

3. The method of embodiment 2, wherein the catalyst is about 5 mol % to about 10 mol % DBU.

4. The method of embodiment 3, wherein the catalyst is about 5 mol % DBU.

5. The method of embodiment 1, wherein the catalyst is acetic acid, trifluoroacetic acid, diisopropylethylamine, or ammonium hydroxide.

6. The method of embodiments 1-5, wherein the deprotecting step (c) further comprises a step of trituration.

7. The method of embodiments 1-6, further comprising recrystallizing or slurrying compound 1.

8. The method of embodiment 7, wherein the recrystallizing is performed at a pH of about 6.0 to about 7.4 and at a temperature of about 50° C. to about 55° C.

9. The method of embodiments 1-8, wherein step (d) is carried out in the presence of a solution comprising acetonitrile.

10. The method of embodiments 1-8, wherein step (d) is carried out in the presence of a solution comprising acetone or tetrahydrofuran.

11. The method of embodiments 1-10, wherein step (b) is carried out in the presence of CeCl₃.

12. The method of embodiments 1-11, wherein the R is a benzoyl group.

13. The method of embodiments 1-12, wherein the palladium catalyst used in step (i) is palladium on charcoal (Pd/C).

14. The method of embodiment 13, wherein the amount of the Pd/C used in step (i) is a catalytic amount of not more than 0.1 part by weight per one part by weight of the compound of Formula IV.

15. The method of embodiment 13, wherein the amount of the Pd/C used in step (i) is 0.025 to 0.05 parts by weight per one part by weight of the compound of Formula IV.

16. The method of embodiments 1-15, wherein step (i) is performed in a mixed solvent comprising ethyl acetate, acetic acid, and water.

17. The method of embodiments 1-16, wherein step (i) is performed under ambient or increased pressure.

18. The method of embodiments 1-17, wherein step (i) is performed under increased pressure of 0.1 to 0.5 MPa.

19. The method of embodiments 1-18, wherein the organic base used in step (iii) is one or more bases selected from the group consisting of DBU, triethylamine, DMAP, and DABCO.

20. The method of embodiments 1-19, wherein the amount of the organic base used in step (iii) is 0.01 to 2.2 moles per mole of the compound of Formula IIIa.

21. The method of embodiments 1-20, wherein the organic base used in step (iii) is DBU.

22. A composition of compound 1:

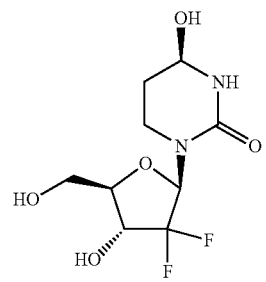

or a salt thereof;
comprising less than 10, 9, 8, 7, 6, or 5 measurable impurities.

23. The composition of claim 24, wherein no impurity is present at a level greater than 0.5 wt %, 0.25 wt %, 0.2 wt %, 0.15 wt %, 0.1 wt %, 0.05 wt %, or 0.01 wt %.

24. A composition of compound 1:

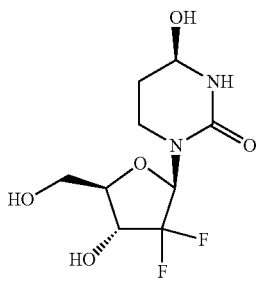

or a salt thereof;
wherein no impurity is present at a level greater than level greater than 0.5 wt %, 0.25 wt %, 0.2 wt %, 0.15 wt %, 0.1 wt %, 0.05 wt %, or 0.01 wt %.

25. The composition of claim 26, comprising less than 10, 9, 8, 7, 6, or 5 measurable impurities.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

What is claimed is:
1. A composition comprising compound 1:

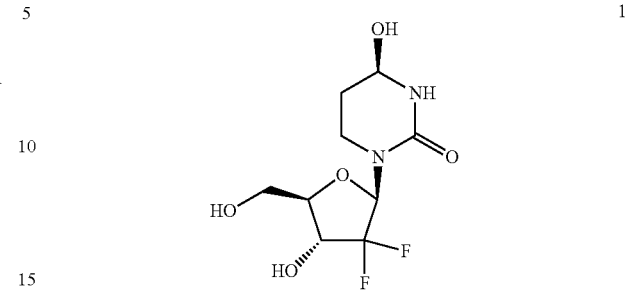

or a salt thereof;
wherein the composition comprises less than 7 measurable impurities, wherein no impurity is present at a level greater than 1.0 wt % of the composition, and wherein compound 1 has a purity of at least 99% by weight of the composition.

2. The composition of claim 1, wherein the composition comprises less than 6 measurable impurities.

3. The composition of claim 1, wherein the composition comprises less than 5 measurable impurities.

4. The composition of claim 1, wherein no impurity is present in the composition at a level greater than 0.5 wt % of the composition.

5. The composition of claim 1, wherein no impurity is present at a level greater than 0.25 wt %.

6. The composition of claim 1, wherein compound 1 has a purity of at least about 99.5% by weight of the composition.

* * * * *

UNITED STATES PATENT AND TRADEMARK OFFICE
CERTIFICATE OF CORRECTION

| | |
|---|---|
| PATENT NO. | : 12,195,496 B2 |
| APPLICATION NO. | : 18/309435 |
| DATED | : January 14, 2025 |
| INVENTOR(S) | : Zuend et al. |

Page 1 of 1

It is certified that error appears in the above-identified patent and that said Letters Patent is hereby corrected as shown below:

In the Specification

Column 5, Line 4: Please correct "±10%, 5%, 1%, 0.5%," to read --±10%, ±5%, ±1%, ±0.5%,--

Column 21-22, Table 4, 1ˢᵗ structure: Please delete the structure and replace with the following:

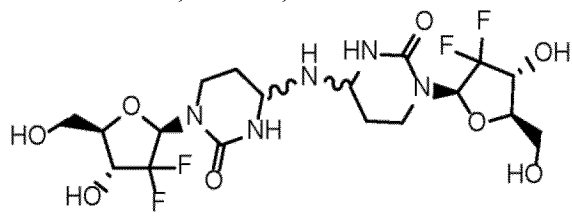

Signed and Sealed this
Twenty-seventh Day of May, 2025

Coke Morgan Stewart
*Acting Director of the United States Patent and Trademark Office*